(12) United States Patent
Mustacich et al.

(10) Patent No.: US 6,490,852 B1
(45) Date of Patent: Dec. 10, 2002

(54) ELECTRICALLY INSULATED GAS CHROMATOGRAPH ASSEMBLY AND METHOD OF FABRICATING SAME

(75) Inventors: Robert V. Mustacich, Santa Barbara, CA (US); John P. Richards, Santa Barbara, CA (US)

(73) Assignee: RVM Scientific, Inc., Santa Barbara, CA (US)

( * ) Notice: Subject to any disclaimer, the term of this patent is extended or adjusted under 35 U.S.C. 154(b) by 0 days.

(21) Appl. No.: 09/693,927

(22) Filed: Oct. 23, 2000

Related U.S. Application Data

(62) Division of application No. 09/090,928, filed on Jun. 5, 1998.

(51) Int. Cl.[7] ................................................. D02G 3/36
(52) U.S. Cl. ............................................................ 57/3
(58) Field of Search ........................ 28/101, 176; 57/2.5, 57/3, 5, 6, 10, 11, 12, 13, 14, 16, 17, 18, 33; 66/3, 4, 9 A; 19/145, 145.3; 242/434

(56) References Cited

U.S. PATENT DOCUMENTS

| | | | | |
|---|---|---|---|---|
| 2,087,303 A | * | 7/1937 | Rosch et al. ............ 174/122 C |
| 4,069,088 A | * | 1/1978 | Cottam ...................... 242/423 |
| 4,112,410 A | * | 9/1978 | Wrob et al. ................ 338/243 |
| 5,678,400 A | * | 10/1997 | Heard ............................ 57/2.5 |

\* cited by examiner

Primary Examiner—John J. Calvert
Assistant Examiner—Shaun Hurley
(74) Attorney, Agent, or Firm—Rosenberg, Klein & Lee

(57) ABSTRACT

An electrically insulated gas chromatograph assembly suitable for high temperature operation in a miniaturized, low power, low thermal mass gas chromatograph instrument is provided. The gas chromatograph (GC) assembly includes a metal capillary GC column (152) having a ceramic fiber insulating layer (156) wrapped about an outer surface thereof. Heater wire (160) is similarly wrapped with a ceramic fiber electrical insulating layer (158). Resistive temperature device (RTD) wire (154) is positioned contiguous an outer surface of insulating layer (156). The composite assembly including insulated capillary GC column (152), insulated heater wire (160), and RTD wire (154), are bound together by applying thereto a spiral wrapped ceramic fiber insulating layer (162).

3 Claims, 7 Drawing Sheets

ELECTRICALLY INSULATED GAS CHROMATOGRAPH ASSEMBLY AND METHOD OF FABRICATING SAME

This application is a divisional of copending application Ser. No. 09/090,928 filed on Jun. 5, 1998.

BACKGROUND OF THE INVENTION

1. Field of the Invention

This invention relates to the field of gas chromatography (GC), and more particularly, is directed to an apparatus and method for fabricating electrically insulated gas chromatograph components for use in gas chromatograph instruments.

The subject invention is further directed to the integration of a plurality of electrically insulated gas chromatograph component members into a gas chromatograph assembly. Of particular importance is that the gas chromatograph assemblies fabricated in accordance with the subject invention find applications in miniaturized, low thermal mass gas chromatography instruments that operate at very high temperatures.

2. Prior Art

In the known prior art systems, integration of miniature heating elements with GC columns has proven to be the most successful approach for achieving miniaturized, low thermal mass, temperature-programmable GC instruments. This approach includes: resistively-heated metal-coated columns; resistively-heated metal-walled columns; small heater plates; internal heater wire; external heater wire; resistively-heated tubing jackets; and, a resistively-heated element with a column in a sheath.

For a resistive-heating element, which runs the length of the column, including the use of the column wall as a heater, special care must be taken to prevent the occurrence of electrical shorts between the resistive-heating element or component member and other conductive components in the GC assembly along the full length of the heating element. Due to the very long lengths of such component member, for example, on the order of 15–30 meters or more, electrical shorts are a constant problem when the component members are packaged and coiled together as an assembly for deployment in the GC instrument. Typically, in the prior art, wire component members are provided with an enamel or other polymeric electrical insulation layer coated or otherwise formed thereover to prevent such electrical shorting. For instance, a coating of high temperature polymer such as polyimide has been provided in some prior art systems.

The aforementioned problem of electrical short formation in the GC column assemblies is exacerbated by the inclusion therein of additional metallic elements, that are coupled to the assembly, for sensing temperature in the assembly for feedback temperature control.

Although it is possible to use the heating element itself as a temperature sensing element, such has proven impractical since the heating element must sense very small resistance changes, for example, on the order of 400 parts per million per degree centigrade (° C.), while at the same time introducing a sufficiently small resistance for the element to function as a heater. Thus, it is standard practice to provide an additional temperature sensor in the assembly which can take the form of a high resistance wire such as platinum, which provides a reproducible substantially linear resistance change with temperature. The co-location of this additional sensing wire or resistance temperature device (RTD) with the heating element or wire provides an adequate solution in one respect since the RTD wire integrates and averages the temperature along the length of the column, however, close placement of the RTD wire with the heating element or wire frequently results in the further occurrence of electrical short formation between these elements and a corresponding failure of the temperature control process.

The problem of electrical short formation is especially acute at the upper end of the standard temperature programming ranges at which capillary GC analytic columns now operate. Typical temperature ranges extending between 250–300° C. are necessary for effective GC analysis, and further, new column materials are offering even higher temperature operation, in excess of 400° C., for extended performance. Most wire insulations, which soften between 100° C. and 200° C., provide inadequate protection from electrical short formation. Further, only the "high temperature" enamel insulations are stable to 250° C., however, even these insulations fail to offer extended life above 250° C., and thus fail to meet temperature requirements in the GC assemblies.

The breakdown of these various insulations at the higher operating temperatures of the capillary column is intensified by the fact that the local temperatures required at the heating element or wire surface typically significantly exceed the required average GC component operating temperatures, since significant thermal conduction and convective losses occur through heating element or wire contact with other components in the GC assembly and the air. Stated otherwise, the heating wire typically runs at a much higher temperature than the average required operating temperature of the GC assembly. This is especially true during the step of temperature programming of the assembly when the heating wire is dissipating the power required to raise the average temperature of the column and other components to a predetermined target temperature. Since the heater wire runs "hotter" than the surrounding components, in order to preserve the integrity of the wire insulation, the maximum average temperature for programming of prior art GC assemblies must be set at a significantly lower level than the temperature at which the integrity of the wire insulation begins to fail or break down. Fast temperature programming of the GC assembly further worsens this problem as insulations on heater wires are easily and quickly destroyed in efforts to rapidly heat other GC components. For example, electrical shorting between enamel insulated heater and RTD wires has been a known problem with prior art tubular jacketed GC assemblies since these assemblies were introduced. With typical RTD control circuits, electrical shorts between the heater and sensor wires may lead to runaway heating conditions.

In addition to the inclusion of both metal heater wires and RTD sensor wires into the GC assembly, another current trend is to further include capillary GC columns made of a metal composition. These metal or steel capillary columns exhibit a robustness exceeding that inherent in the fused silica capillary GC columns, thus, such robust columns are of special interest for use in ruggedized instruments such as field portable GC instruments.

Due to the aforementioned problems associated with electrical shorting between heater wires and RTD wires, it has not previously been practical or indeed advisable to introduce steel capillary GC columns into wire-heated GC assemblies unless the maximum operating temperatures and temperature programming rates are kept sufficiently low so as to protect the integrity of the electrical insulation layers. Even in such limited and conservative operational circumstances, the likelihood that electrical shorts will form is still large since typical polyimide wire insulation coating is only a few thousandths of an inch thick, even for supposed "heavy" coating "builds." This structural limitation provides insufficient insulation integrity under numerous common situations which leads to frequent electrical shorting. For instance, the insulation films are so thin that manufacturing defects affecting the thickness of the insulation, stress experienced in the insulation during handling of the GC instrument components, bending of the insulation, brittleness of the coating due to age and repetitive cyclic heating, all contribute to insulation layer failures and consequent operational shorting of the metal GC columns with the other metal components. Thus, the commercially available wire insulations have not been found to meet the operational requirements of the various GC assemblies and their applications. Further intensifying these problems is the fact that due to the much greater thermal mass of steel capillary GC columns, as compared to the quartz or silica GC columns, more power is required to perform temperature programming which, as discussed previously, generates higher surface temperatures for the variety of heating elements included in the assembly.

In practice, the failure of the polyimide coated heater wire is demonstrable. Such failure occurs even when the polyimide coating is specified as a "quad" build, that is, a thick coating, rated to survive 1,000 hours at 300° C. The coating quickly fails due to the high local temperatures required at the wire surface to meet overall 300° C. GC temperature program requirements, as described above.

SUMMARY OF THE INVENTION

In view of the numerous shortcomings of the prior art systems, it is an object of the subject invention to provide an apparatus and method for fabricating an electrically insulated gas chromatograph component member, and an assembly of such component members suitable for use in miniature low thermal mass gas chromatograph instruments operating at high temperatures.

It is a further object of the subject invention to fabricate electrically insulated gas chromatograph assemblies wherein small heaters and heated components required for gas chromatograph operation are provided in a compact, closely coupled arrangement thus facilitating their integration into miniature gas chromatograph instruments.

Another object of the subject invention is to apply electrical insulating layers to the surfaces of various gas chromatograph component members, where the electrical insulating layers maintain their electrical insulating integrity at high temperature operation, while at simultaneously providing adequate thermal conduction between the various integrated, closely coupled, gas chromatograph component members present in the assembly.

Another object of the subject invention is to render practical the use of metallic component members, such as steel capillary gas chromatograph columns in miniature gas chromatograph assemblies or instruments.

In accordance with the subject invention, a method is provided for applying an electrical insulating layer to the surface of a gas chromatograph (GC) component member. The method includes providing at least one elongate GC component member extending in a predetermined direction, and providing at least one dispensing mechanism for dispensing a plurality of fibers therefrom. As the elongate GC component member is progressively advanced along the predetermined direction, the dispensing mechanism is rotatively displaced about the progressively advancing GC component member. Responsive to this rotative displacement, the dispensing mechanism dispenses the plurality of fibers therefrom which are progressively wound around the outer surface of the GC component member.

A gas chromatograph (GC) column assembly fabricated in accordance with the subject invention includes a first GC component member which has a first ceramic roving insulation layer wrapped about the exterior surface of the first GC component member. A second GC component member adjacently displaced from the first GC component member, where the first GC component member is a capillary GC analytic column member, and the second GC component member is a heating wire.

DESCRIPTION OF THE PREFERRED EMBODIMENTS

Figure 1:
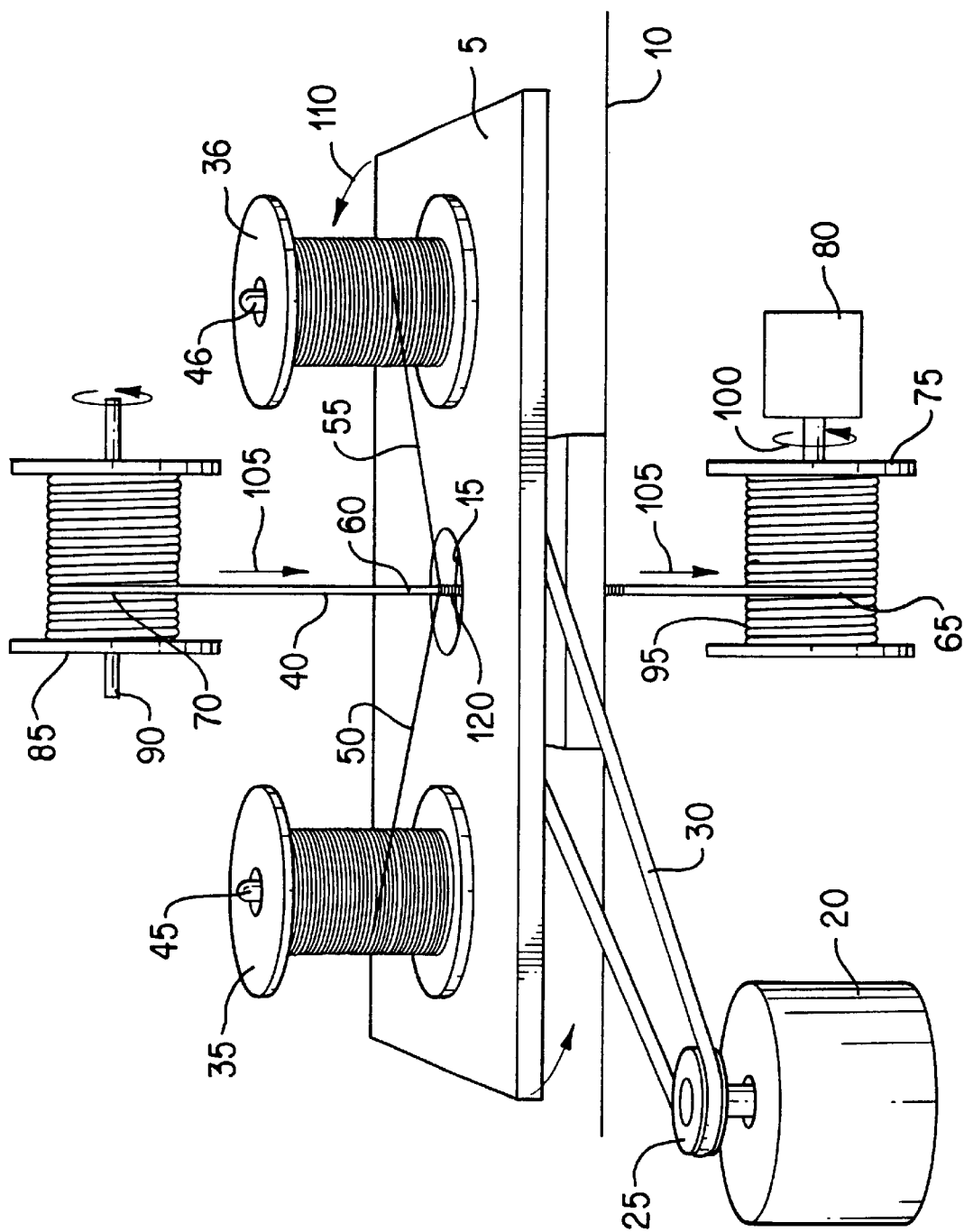
FIG. 1 is a perspective view showing the wrapping apparatus of the subject invention used to fabricate electrically insulated gas chromatograph component members in accordance with the method of the subject invention.

In the subject invention, an electrically insulating layer is applied to the surface of various Gas Chromatograph (GC) assembly component members, such as the capillary GC analytic column, heater wires, and resistive temperature device (RTD) wires, as well as various combinations and sub-combinations thereof. The object is to enable close integration of these various GC component elements or members into a miniature, low thermal mass GC assembly capable of achieving higher operational temperatures with greater immunity to electrical shorting than is possible with the known prior art techniques for electrically insulating the various GC component members. Application of the subject invention greatly extends and improves the performance of GC assemblies, particularly low power GC assemblies, as small heaters and heated components required for GC operation are successfully integrated. Further, the subject invention renders practical the inclusion of metallic components such as steel capillary GC columns in miniature GC assemblies.

The insulation layer of the subject invention advantageously meets the contrary twin objectives of first preventing electrical shorting between the various integrated GC components even at high temperature cycling while secondly, maximizing the heat conducted between the heating element and the other elements or components to be heated in the GC assembly. These two objectives are disparate since, in the prior art, high temperature electrical insulation tends to minimize heat conduction between the insulated components or wires and other components. Nevertheless, the subject invention strikes a successful balance between these two opposing goals.

The subject invention reconciles the goal of electrical short prevention at very high operational temperatures with that of maximizing heat conduction between insulated elements through utilization of an insulating layer comprising a material stable to high temperatures, while minimizing the requirement of insulation thickness and mass to thus permit sufficient thermal conduction. Accordingly, the subject invention uses an insulating layer formed of a ceramic fiber composition that maintains suitable electrically insulating qualities under very high temperature conditions of, for example, greater than 1,000° C. Woven or braided fabric insulations, whether glass or ceramic-based, are typically far too thick to be useful in miniature GC assemblies, since heat conduction is substantively impeded by insulation layers comprised of such dense material, there are on the other hand, precursors to certain high temperature ceramic threads available which can be used in accordance with the subject invention to successfully fabricate electrically insulating layers that meet the twin objectives described previously.

In particular, in the subject invention an electrical insulating layer for a GC assembly component member is formed of a ceramic composition, where the ceramic composition comprises a ceramic roving or thread which is wound or spirally wrapped around the outer surface of the GC component member. In the context of the subject invention, the term "roving" refers to a loose assemblage or plurality of substantially continuous and co-extensive (parallel), untwisted and unbraided fibers. For example, one such roving is commercially available under the trade designation "NEXTEL Ceramic Fiber" from the 3M Company. An exemplary roving includes approximately 200 untwisted ceramic filaments, each having a cross-sectional dimension of approximately 8–12 microns. When the ceramic roving is wound or spirally wrapped about a GC component member, the individual fibers therein spread across the surface of the wrapped component member to thus provide an electrically insulating layer characterized by 1) minimized thickness and thermal mass, and 2) compositional integrity at very high temperatures, thus attaining the twin objectives of acceptable thermal conductivity and excellent electrical insulative effectiveness at high temperature, as stated above.

Referring to FIG. 1, in accordance with the present invention, an apparatus is provided for applying the ceramic roving insulation layer to the outer surface of a GC component member. As will be discussed more fully in following paragraphs, exemplary GC component members for use in a GC instrument include, but are not limited to, capillary GC columns, heater wires, RTD wires, preconcentrators, transfer lines, or combinations and sub-combinations thereof.

The apparatus includes a rotatable plate or rotatable support member 5 that is rotatably coupled to a base plate 10. Both rotatable support member 5 and base plate 10 have formed therethrough a centrally disposed aperture 15. A variable speed motor 20 is coupled by way of pulley 25 and drive belt 30 to rotating plate 5 whereby variable speed motor 20 rotatably displaces rotating plate 5 about an axis line of rotation passing through aperture 15. Other suitable mechanism for rotatably displacing the plate 5 may be used, including a variable speed motor coupled to rotating plate 5 through a series of gearing mechanisms, clutches and/or pulleys. Further, a variable speed motor having a hollow shaft formed therethrough, which shaft coincides with aperture 15, can be used to directly drive the rotating plate.

Mounted to an upper surface of the rotating plate 5 is a pair of fiber dispensing spools 35,36, each spool carrying ceramic fiber roving thereon which fiber is dispensed from the spool for application to the surface of GC component member 40. The fiber dispensing mechanisms need not be limited to spools, but other known dispensing mechanism which may be used as long as they meet the operational/functional requirements described herein.

Spools 35,36, as shown, are themselves mounted or more particularly, rotatively coupled, to the upper surface of rotating plate 5 by way of respective spindle mechanisms 45,46, about which spindles the spools rotate as fibers are dispensed therefrom. Although a pair of spools 35,36 are shown mounted to rotatable plate 5 at opposing sides of aperture 15, effective application of an insulating layer to the surface of GC component member 40 requires only one fiber dispensing spool. It should be appreciated that one, two or more fiber dispensing spools can be mounted to rotatable plate 5, in whatever predetermined positional arrangement is required to effect a desired coverage density for the insulating layer that is to be applied to the surface of GC component member 40.

As shown in FIG. 1, dispensed ends 50,55 of ceramic roving or fibers extend respectively from fiber dispensing spools 35,36 and engage an outer surface of elongated segment 60 of GC component member 40, to which outer surface the ceramic roving electrical insulating layer is to be applied. Each dispensed end 50,55 of ceramic roving has an end-portion thereof at least partially wrapped around the outer surface of the GC component 40.

GC component 40 includes a lower portion 65 wound around a motorized take-up spool 75, the motorized spool being rotatively driven by a controllable, variable speed motor 80. An upper portion 70 of GC component member 40 is wrapped about a feed-spool 85 frictionally coupled to spindle 90 for free-wheeling (non-driven) rotation of feed-spool 85 about spindle 90. Thus, GC component member 40 need only be sufficiently flexible so as not to be damaged when stored on these spools. Extending between lower and upper portions 65,70 of GC component member 40 is an elongated segment 60 of GC component member 40.

It should be appreciated that take-up spool 75, variable speed motor 80, feed-spool 85, and spindle 90 are merely representative of numerous other equally effective embodiments, the variations of which are not important to the inventive concept of the subject invention with the exception that they are enabled to accomplish the purposes and objectives intended. As an example, variable speed motor 80 may be coupled to take-up spool 75 through gears, clutches and/or drive belts and chains. Further, any other rotative coupling mechanisms known in the prior art may replace the spindle 90 as long as it permits frictional rotative coupling of feed-spool 85. Even further, wrapping drum 95 of take-up spool 75 may assume various geometrical configurations suitable to the application. If a plurality of GC component members are to be wrapped simultaneously together using the apparatus shown, additional sets of take-up spools and feed-spools, and their associated GC component members, may be included alongside the set already shown in FIG. 1.

Figure 2:
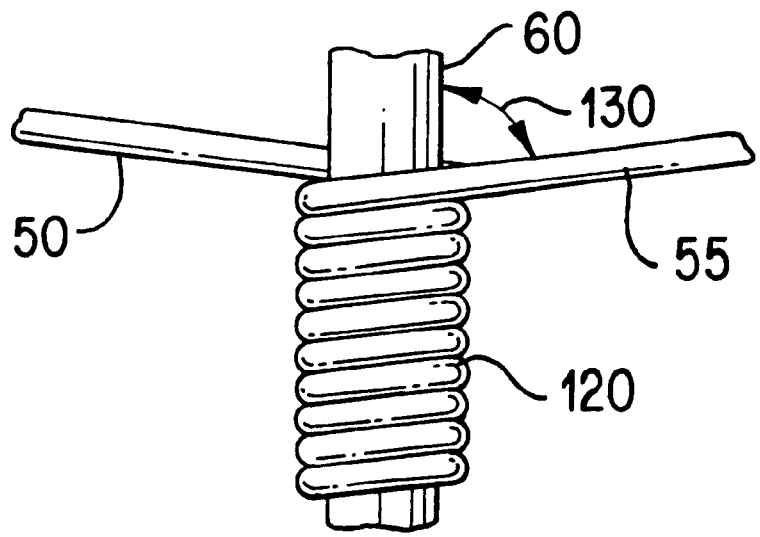
FIG. 2 is an enlarged perspective view of the wrapped portion of the gas chromatograph component member shown in FIG. 1.

Referring to FIGS. 1 and 2, the method by which the ceramic roving is wound or spirally wrapped around the outer surface of GC component member 40 includes an initial set-up where a free end of GC component member 40, initially stored around feed-spool 85, is fed through centrally disposed aperture 15 and is at least partially wrapped around lower take-up spool 75, as at 65. Subsequently, end-portions of dispensed ends 50,55 of ceramic roving are at least partially spirally wrapped or wound around the outer surface of elongated segment 60 of GC component member 40 extending between the upper and lower spools.

A progressive winding operation is initiated by a take-up spool 75 which is rotatively driven by variable speed motor 80 in the direction shown by arrow 100 thus causing elongated segment 60 of GC component member 40 to progressively advance, from the feed-spool 85 toward (and onto) take-up spool 75, along the direction shown by arrows 105. The frictionally biased rotative displacement of feed-spool 85 about spindle 90 ensures that elongated segment 60 of GC component 40 is kept under a low tension load between the upper and lower spools, to thus maintain its elongate form as GC component member 40 is unwound from feed-spool 85 and wound onto take-up spool 75.

Simultaneous with the progressive advancement of GC component member 40 down through centrally disposed aperture 15, variable speed motor 20 rotatively displaces rotatable support member 5 about the axis line of rotation passing through aperture 15, in the direction as shown by arrow 110. As rotatable support member 5 is rotatively displaced about elongated segment 60 of GC component member 40, so too are both fiber dispensing spools 35,36 correspondingly rotatively displaced about this axis line of rotation. It is seen that spools 35,36 also rotate about their respective mounting spindles 45,46. Since end portions of dispensed ends 50,55 of ceramic roving are at least partially wound or spirally wrapped about the outer surface of elongated segment 60 of GC component member 40, both fiber dispensing spools 35,36 further continuously dispense ceramic roving to the outer surface of elongated segment 60, responsive to their rotative displacement about the GC component member. Stated otherwise, the ceramic roving is drawn-off of each spool as rotatable support member 5 is rotatably displaced, and responsive to this dispensing action, fiber dispensing spools 35,36 spin about their respective spindles 45,46. In this manner, the outer surface of GC component member 40 is progressively spirally wrapped with a layer of ceramic fiber or roving as GC component member 40 progressively advances from feed-spool 85 onto take-up spool 75.

Referring to FIG. 2, an enlarged view of the wrapped portion of elongated segment 60 reveals that, as dispensing spools 35,36 rotate along with rotatable plate 5, dispensed ends 50,55 tangentially engage the outer surface of elongated segment 60 of GC component member 40 at opposing sides thereof. As the ceramic roving is drawn from each spool, it becomes spirally wrapped about the outer surface of GC component member 40. The result being that the outer surface of GC component member 40 becomes covered by electrical insulating layer 120 which consists of a plurality of spiral windings of ceramic roving. Note that in FIG. 2, pitch angle 130, the angle at which insulating fiber is spirally wrapped about the surface of component member 40, is defined as the angle subtended between a length of elongated segment 60 and that portion of dispensed end 50 (or 55) of fiber tangentially engaging the outer surface of elongated segment 60.

To maximize the effectiveness of the apparatus in applying the insulating wire to the outer surface of the GC component member, and to optimize the coverage density of the ceramic roving over the surface of the GC component member, the apparatus in FIG. 1, and the method by which it is used, allows for certain adjustments to be made in the overall operation. One parameter that is controlled during the component member wrapping operation is the tension under which the dispensed ends 50,55 are applied to or wound around the outer surface of the GC component member. To account for this parameter, the apparatus provides a mechanism by which a predetermined tension can be established in the ceramic roving as it is wrapped about the GC component member. As discussed previously, fiber dispensing spools 35,36 rotate about respective spindles 45,46 as fiber is dispensed from the spools and onto the GC component member. Thus, by adjusting the level of friction existing between spindles 45,46 and their respective spools 35,36, that is, by adjusting a braking force between the spindles and their spools, a predetermined tension force can be established or controlled under which the component member is wrapped by the roving.

Alternatively, wrapping tension can be adjusted by a corresponding adjustment to the magnitude of friction existing at the interface between the upper surface of rotating plate 5 and the bottom portion of spools 35,36 resting thereon. For instance, by simply increasing the weight of spools 35,36 the level of friction may be increased, thus establishing a higher predetermined level of tension force under which the ceramic roving is applied to the surface of the GC component member. Other mechanisms well known in the art can be used for controlling the friction force that is exerted against the rotation of the rotating spools 35,36 to thus establish a predetermined level of tension in the ceramic roving insulation layer. In summary, one method for adjusting the coverage density of the insulating layer, or more particularly, the coverage density of the ceramic fiber wound around the outer surface of the GC component member, is to establish a corresponding predetermined level of tension under which the ceramic fibers are wrapped around the GC component member.

Another operational parameter important in the control of the coverage density of the insulating layer involves the control of both the angular speed at which rotatable support member 5 is rotatively displaced, and the linear speed at which GC component member 40 is progressively advanced in the direction of arrows 105 during the wrapping operation. Particularly, by establishing a predetermined ratio of angular speeds between motor 20, which establishes the angular speed of rotatable support member 5, and motor 80, which determines the angular speed of take-up spool 75 and correspondingly the linear speed of elongated segment 60 along the direction of arrows 105, the insulating layer coverage density can correspondingly be adjusted or controlled. By varying the aforementioned speeds, pitch angle 130, as seen in FIG. 2., at which the fiber is spirally wrapped about the outer surface of the component member, is correspondingly varied. Accordingly, adjusting speeds to decrease or reduce pitch angle 130 decreases fiber coverage density. Alternatively, speed ratios that increase pitch angle correspondingly increase coverage density.

It should further be appreciated that coverage density varies as a combined function of the speed ratio, as previously described, and the diameter of the member being wrapped. Thus, elongate member diameter is a factor that should be considered in controlling the speed ratio, to establish a predetermined coverage density.

In summary, the coverage density of the insulating layer as applied to the outer surface of the GC component member, can be controlled by the apparatus and method of the subject invention. Particularly, by adjusting the roving tension, the travel speed of the GC component member, and the angular speed of the dispensing spools as the component member is progressively wrapped, the coverage density of the insulating layer is correspondingly adjusted. Additionally, coverage density of the insulating layer may be increased by applying more than one layer of fiber to the GC component member. For instance, the component member can be wrapped once, twice or three times—or as many additional times as are required by the application.

Additional care must be taken to ensure a good quality wrapping of the fiber. If wrapping occurs under too high a tension, undesirable splitting and fraying of the fiber can occur as the fiber is bent around the outer surface of the elongate member. Typically, the smaller is the diameter of the elongate member being wrapped, the more prevalent is the splitting and fraying of the fiber as it is wrapped about the member under tension. Thus, the ability to set the tension at a predetermined level commensurate with the diameter of the elongate member is important in achieving a high quality wrap for the insulating layer as well as in establishing a desired coverage density therefore. In fact, appropriate selections for the speed ratio and resulting pitch angle of the wrap, and tension of the wrap, are each a function of the diameter of the component being wrapped.

It should be appreciated that in FIG. 1, although a unitary rotatable support member 5 is shown having a centrally disposed aperture 15 formed therethrough, other functionally equivalent embodiments can equally suffice to perform the wrapping operation as long as the fiber dispensing mechanisms or spools provided, are rotatively displaced about the outer surface of an elongated GC component member which is displaced radially inward with respect to the spools is progressively advanced along a predetermined direction. This predetermined direction need not necessarily be perpendicular to the plane of rotation of the dispensing spools, and the position of the elongated segment 60 need not be coincident with the axis line of rotation about which the spools are rotatively displaced. Further, it is not necessary to provide a unitary rotatable support member 5 as is shown in FIG. 1. A pair of rotatable support members may be provided in spaced relation each to the other with each of these rotatable support members supporting a fiber dispensing mechanism upon an upper surface thereof.

The apparatus and method described above can be used in the fabrication of a broad range of electrically insulated, low power GC assemblies. The following series of embodiments are exemplary of this broad range of possibilities, and in no way limit the number of further embodiments that can be produced or fabricated using the apparatus and method described previously. Typically, the following embodiments have actually been fabricated in accordance with the techniques of the subject invention and operationally tested. Consequently, specific lengths, diameters and compositions of the various GC component members and the roving included in the fabricated assemblies have been established and are provided herein. Such specifics are exemplary only and are not intended to limit in any way the applications of the subject invention, but rather, the subject invention is equally applicable to all GC assemblies including therein component members functionally equivalent, and arranged or integrated similarly, to those provided in the embodiments to be described.

Further, in each of the following embodiments, the specified insulating layers comprise a Nextel ceramic roving, such as Nextel 600 Denier (D) roving. However, a wide variety of ceramic fiber rovings may be used to insulate the GC component members, as long as it permits the application of a good quality insulation layer to the surface of the GC component member, meets the operational temperature requirements and permits acceptable thermal conduction between the integrated GC component members.

Figure 3:
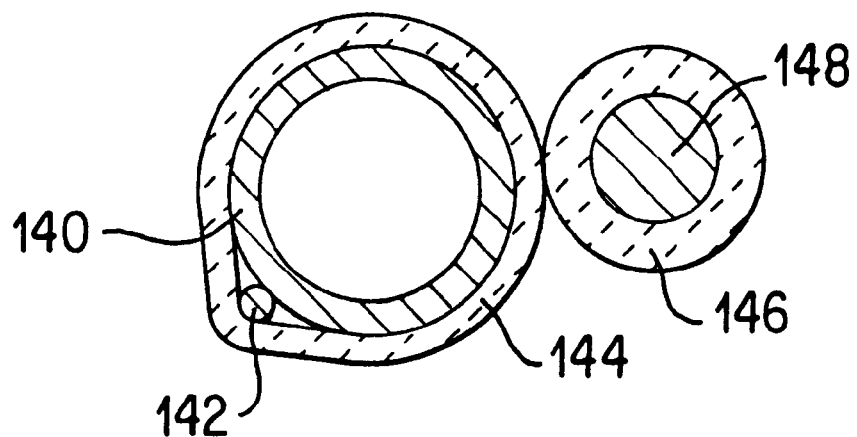
FIG. 3 is a front, cross-sectional view of a first embodiment of a gas chromatograph assembly fabricated using the apparatus shown in FIG. 1.

Referring to FIG. 3, a first embodiment of a low power GC assembly includes a first GC component member 140 that is a non-metallic capillary GC column made from, for example, fused silica, and which has an inner diameter (ID) of, for example, 0.25 mm. An RTD wire 142 made of, for example, platinum and having a diameter of, for example, 0.002", is in contacting relation with GC column 140. A first ceramic roving insulating layer 144 consisting of, for example, Nextel 600 D ceramic roving, is applied to the outer surface of GC column 140 and RTD wire 142.

The insulating layer is applied to the GC column 140 and RTD wire 142 using the apparatus of the subject invention, and comprises a slight spiraling, of approximately 1 turn per inch, of the ceramic roving as applied to the surface of column 140. Also included in the GC assembly is a second GC component member, namely, heater wire 148, made of, for example, nickel, and having a length of, for example, 5', and a diameter of, for example, 0.008". A second electrical insulating layer 146 of ceramic roving is applied to the outer surface of heater wire 148.

The assembly of FIG. 3 was fabricated using the winding apparatus of FIG. 1. The assembly was coiled and then used in a small, low power GC assembly. The coiled GC assembly was temperature programmed over a temperature range extending between ambient and 400° C., at a variety of different speeds. Although the ceramic roving electrical insulation maintained its integrity throughout testing even at the highest temperatures, it is interesting to note that the polyimide insulation provided on nickel heater wire 148 was burnt away without consequence during the temperature programming cycles. That is, operational destruction of the standard polyimide insulation during operation of the GC assembly was of no consequence due to the presence of the ceramic fiber electrical insulating layers which maintained their integrity throughout the tests.

Figure 4:
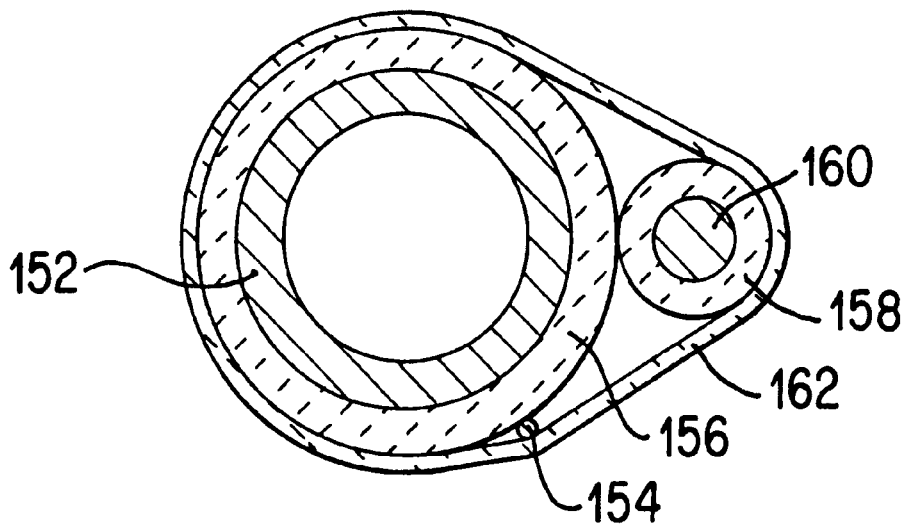
FIG. 4 is a front, cross-sectional view of a second embodiment of a gas chromatograph assembly fabricated using the apparatus shown in FIG. 1.

Referring to FIG. 4, in a second embodiment of a GC assembly, capillary column 152, formed of a metallic composition such as steel, has an ID of, for example, 0.28 mm, and a length of, for example, 15 m. GC column 152 is wrapped with a ceramic fiber insulating layer 156 in accordance with the method and apparatus of the subject invention shown in FIG. 1, using for example, the Nextel 600 D ceramic roving. A 15 m length of 0.008" diameter nickel heater wire 160 is similarly wrapped with electrically insulating ceramic fiber layer 158. During fabrication, RTD wire 154 is positioned contiguous an outer surface of insulating layer 156, and using the apparatus and method for winding of the subject invention, the composite assembly including insulated GC assembly 152, heater wire 160, and RTD wire 154, are bound together by applying thereto a spiral wrapped ceramic fiber insulating layer 162 having a spiral wrap rate of, for example, 1 turn per inch. Next, the entire assembly is coiled to a diameter of 3.5" and wrapped with aluminum foil.

The resulting assembly, including the component members as shown in FIG. 4, was tested operationally and, in addition, handled numerous times during these testing procedures. No electrical shorting, or any other difficulties were observed throughout this test period. During temperature programming of the assembly, power consumption was measured at temperatures of 180° C. and 300° C. Considerable power was required for temperature programming this assembly due to the relatively large mass of the steel capillary tubing of capillary column 152. For instance, at 60° C. per minute, a temperature rise from 40° to 180° C. requires a power of approximately 27 watts, compared to a required power of approximately 10 watts for a fused silica column assembly responding at the same rate. It should be appreciated that even though this increased power requirement is indicative of the presence of much higher local temperatures at the surface of heater wire 160, the thin, uniformly spread layer of ceramic fiber insulation throughout the assembly, as along the column and heater wire, serves to protect other components in the assembly, and also to advantageously increase the uniformity of the local temperatures at the capillary GC column.

Figure 5:
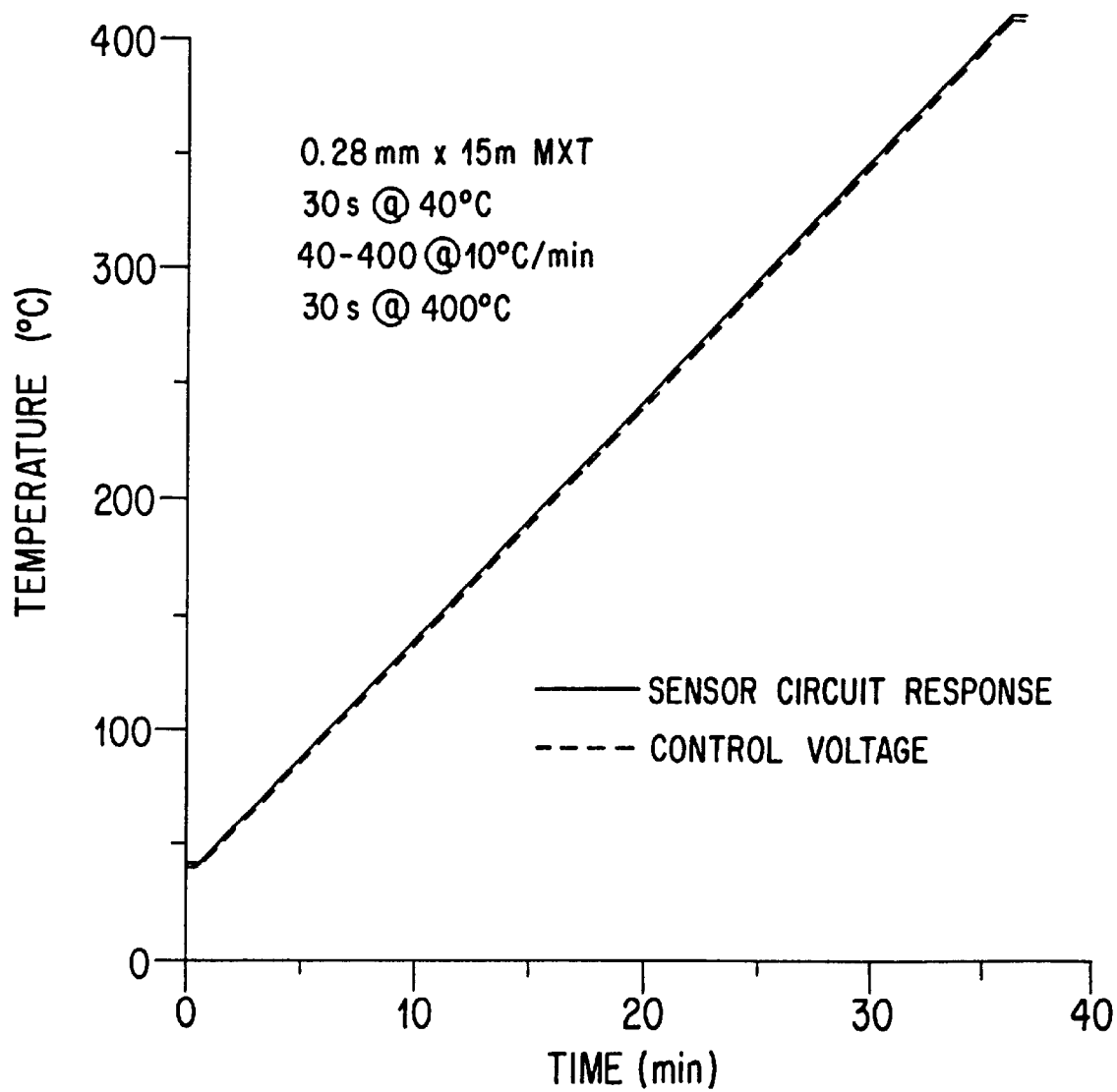
FIG. 5 is a graph illustrating the temperature/time profile of the gas chromatograph assembly of FIG. 4.

Referring to the temperature-time graph of FIG. 5, an exemplary temperature recording is illustrated of RTD temperature sensor 174 during a temperature programming run of the GC assembly of FIG. 4. Notably, the GC assembly was repeatedly temperature programmed up to 400° C. with no formation of electrical shorting. The ceramic fiber insulating layer, having a temperature rating of 1200° C., far above the maximum temperatures at which the GC assembly was operated, maintained its integrity throughout testing.

Figure 6:
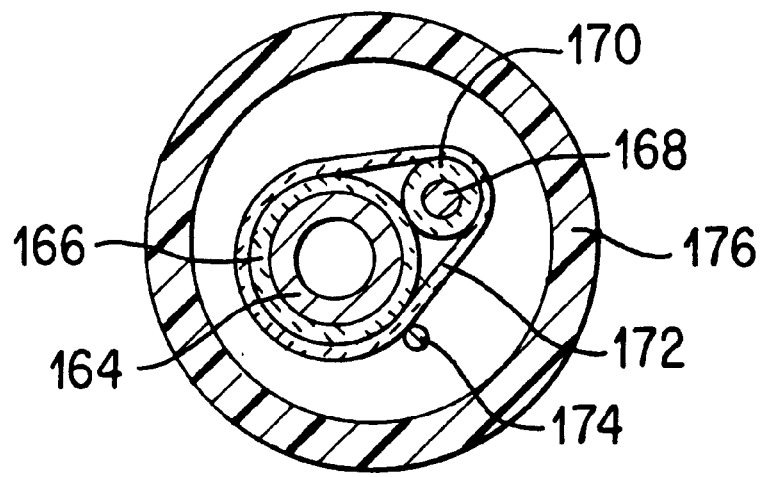
FIG. 6 is a front, cross-sectional view of a third embodiment of a gas chromatograph assembly fabricated using the apparatus shown in FIG. 1.
Figure 7:
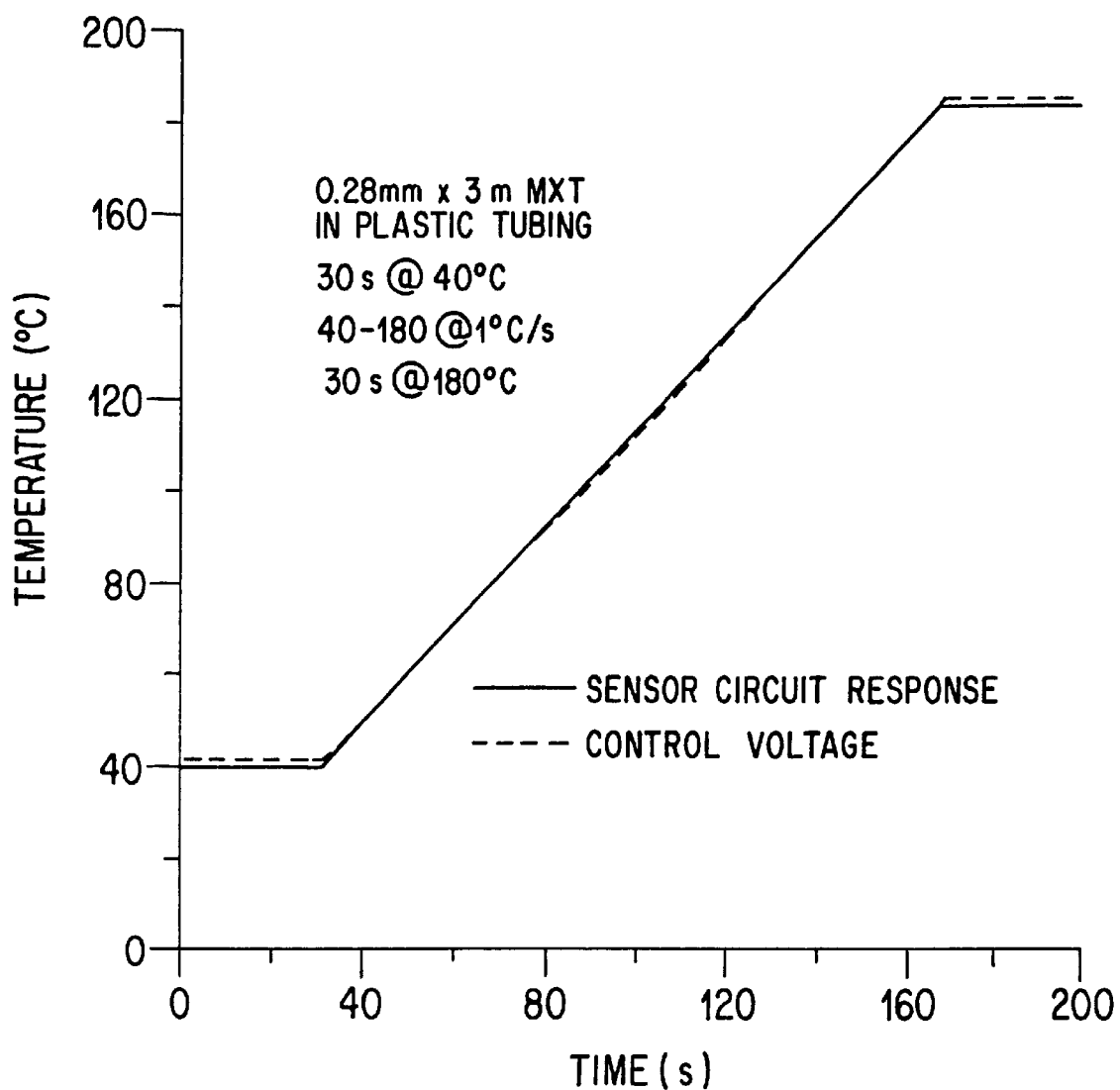
FIG. 7 is a temperature/time graph illustrating a temperature programming cycle of the apparatus shown in FIG. 6.

Referring to FIG. 6, a third embodiment of a miniature GC assembly is shown where a 3 m length of 0.28 mm ID steel capillary column 164 is wrapped with a ceramic roving insulating layer 166. A 3 m length of 0.006" diameter nickel heater wire 168 is similarly wrapped with ceramic roving insulating layer 170. The wrapped GC column 164 and wrapped heater wire 168 are bound together with a loosely wrapped ceramic roving insulating layer 172. This binding layer is applied to the inner member by wrapping the inner members together with the winding apparatus of the subject invention. A 3 m length of platinum RTD wire 174 is spirally wrapped around the inner assembly (the GC column heater wire and surrounding insulating layers), with a slight spiraling pitch. The resulting assembly is placed within the inner bore of a 3 m length of 13 gauge thin-walled Teflon tubing 176. This GC assembly was fabricated using the techniques of the present invention and then temperature programmed to 180° C. at a rate of 60° C./sec. Referring to FIG. 7, an exemplary recording of RTD temperature sensor 174 during a temperature programming run is illustrated. No electrical shorts occurred as the insulating layers maintained their integrity.

In a straightforward variation of the configuration shown in FIG. 6, Teflon tubing 176 can be replaced by a resistively-heated metal outer tube. In this configuration, the heated outer tube itself heats the steel capillary column disposed therein thus obviating the need for heater wire 168. Further, wrapping a ceramic roving insulating layer around the inner assembly disposed within the outer tube, prevents electrical short formation between the inner assembly components and the inner surface of the resistively heated outer tube.

In addition to the fabrication of capillary GC analytic columns using the techniques and materials of the subject invention, other miniature GC assemblies can be fabricated with all of the attendant advantages described in relation to the previously discussed assemblies. For instance, miniature vapor preconcentrators, another small GC component, can benefit from the subject invention. Miniature vapor preconcentrators include a small tube containing an adsorbent therein. The tube is rapidly heated to release any adsorbed vapors for subsequent analysis by a chromatograph. For vapor sampling in a small GC instrument, a small adsorbent preconcentrator can be fabricated in-line with the GC column using standard stainless steel gas lines or glass tubing. One prior art approach relies on the use of layers of supposed "high temperature" epoxy glues to insulate and bind heating wire and sensing wire windings around a small steel tube which is packed with the adsorbent described above. This prior art approach is problematic in that the glues used to bind the components together eventually decompose or crumble, thus contributing to the undesirable development of electrical shorts between the various components originally bound together with the glue. This problem is exacerbated by the fact that the insulation on the wires, such as polyimide coatings, has also typically been destroyed or burnt away during high temperature and extended use of the assembly.

The subject invention provides a solution to these prior art shortcomings wherein ceramic fiber insulating layers are used to electrically insulate the heating wire and the RTD wire present in the adsorbent preconcentrator assemblies. For example, referring to FIG. 8, in a fourth embodiment of a GC assembly, the preconcentrator depicted includes a 0.12" diameter glass tube 180 containing an adsorbent material 182 therein. Approximately 10" of a 0.01" diameter Nichrome heater wire 184 is wrapped around a short segment, on the order of 1.5" in length, of glass tube 180. A ceramic roving electrically insulating layer 186 is next wrapped about the heater wire 184 such that the heater wire 184 is substantially covered by the insulating layer. A 3' length of 0.002" diameter polyimide-insulated platinum RTD wire 188 is wound about the entire assembly, and is in contact with the outer surface of insulating layer 186.

Figure 8:
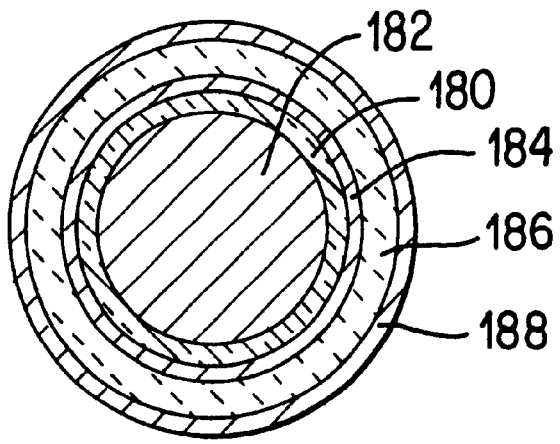
FIG. 8 is a cross-sectional view of a fourth embodiment of a gas chromatograph assembly fabricated using the apparatus shown in FIG. 1.

The preconcentrator assembly of FIG. 8, fabricated in accordance with the techniques of the subject invention, was installed in a small GC assembly injection system, and during operational tests demonstrated rapid heating thereof with the desorption of vapors into the gas streams for subsequent GC analysis. During routine use and testing of the preconcentrator assembly, no electrical shorting occurred between either the sensor or heater wires, and no mechanical failures were observed or discovered in the materials or ceramic fiber insulation used in the assembly. In another embodiment of the preconcentrator assembly that has been successfully demonstrated, glass tube 180 is replaced by a metal tube having a ceramic insulating layer wrapped thereabout. A nichrome heater wire having a ceramic insulating wire wrapped thereabout is wound around the insulated metal tube. An RTD wire can be provided either between the insulated heater wire and the insulated metal tube, or as a winding about the outside of the heater wire.

The subject invention is further advantageously directed to transfer lines used in GC assemblies. Transfer lines in a variety of GC assemblies essentially comprise conduits coupled to the input and/or output end of the capillary GC analytic column for carrying therein the chemical vapors that enter and exit the GC analytic column, respectively. Whether the transfer line is coupled to the GC analytic column at the injection end or at the exit end thereof, from where the gases are transferred to a subsequent detector, the transfer lines carrying the analyte samples, typically in a carrier gas such as helium, must be heated to prevent condensation losses of the chemical vapors on the inner walls of the transfer line or within the other plumbing and attachment/coupling components of the GC assembly such as connectors. The subject invention directs itself advantageously to the fabrication of such transfer lines provided in miniature GC assemblies wherein the transfer lines can be either continuously or intermittently heated.

Figure 10:
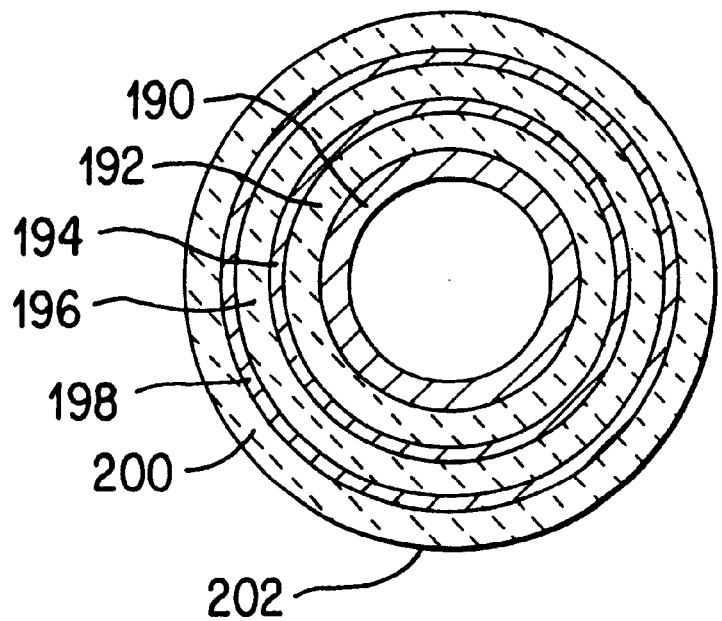

Referring to FIG. 10, in a fifth embodiment of a GC assembly, such a transfer line is provided which operates as a "flash heated" injector line for injecting the vapors into a capillary GC analytic column. The "flash heated" injector line is used to heat a connection between a preconcentrator, as described with reference to FIG. 8, and a low power GC column formed in a toroidal configuration. The techniques of the subject invention as used in this transfer line advantageously avoid adverse side effects known in the prior art which include the undesirable additional heating of the GC toroid and the requirement of excessive power which is undesirable in a miniature GC assembly environment. In operation, to conserve power, the transfer line is rapidly heated intermittently, that is, it is heated only during the vapor injection phase of the GC assembly operation.

As shown in the figure, the transfer line includes an inner steel capillary GC column 190 having a length of approximately 3.5" and ID of approximately 0.28 mm. Ceramic fiber insulating layer 192 is wrapped around column 190. Approximately 10" of 0.010" diameter nichrome heater wire 194 is wrapped or wound around the insulated column 190. Alternatively, the heater wire can itself be wrapped with an insulating layer prior to being wound around column 190. Since, in this alternative configuration, the heater wire is insulated, column 190 may be provided with, or even without, an insulating layer wrapped thereabout. A second layer 196 of ceramic fiber insulation is wrapped about the windings of heater wire 194. Next, RTD wire windings 198 are wrapped about or over insulating layer 196. Finally, the outer surface of ceramic fiber insulating layer 200 is covered with aluminum foil which has the effect of enhancing the uniformity of heat throughout and along the assembly.

Figure 9:
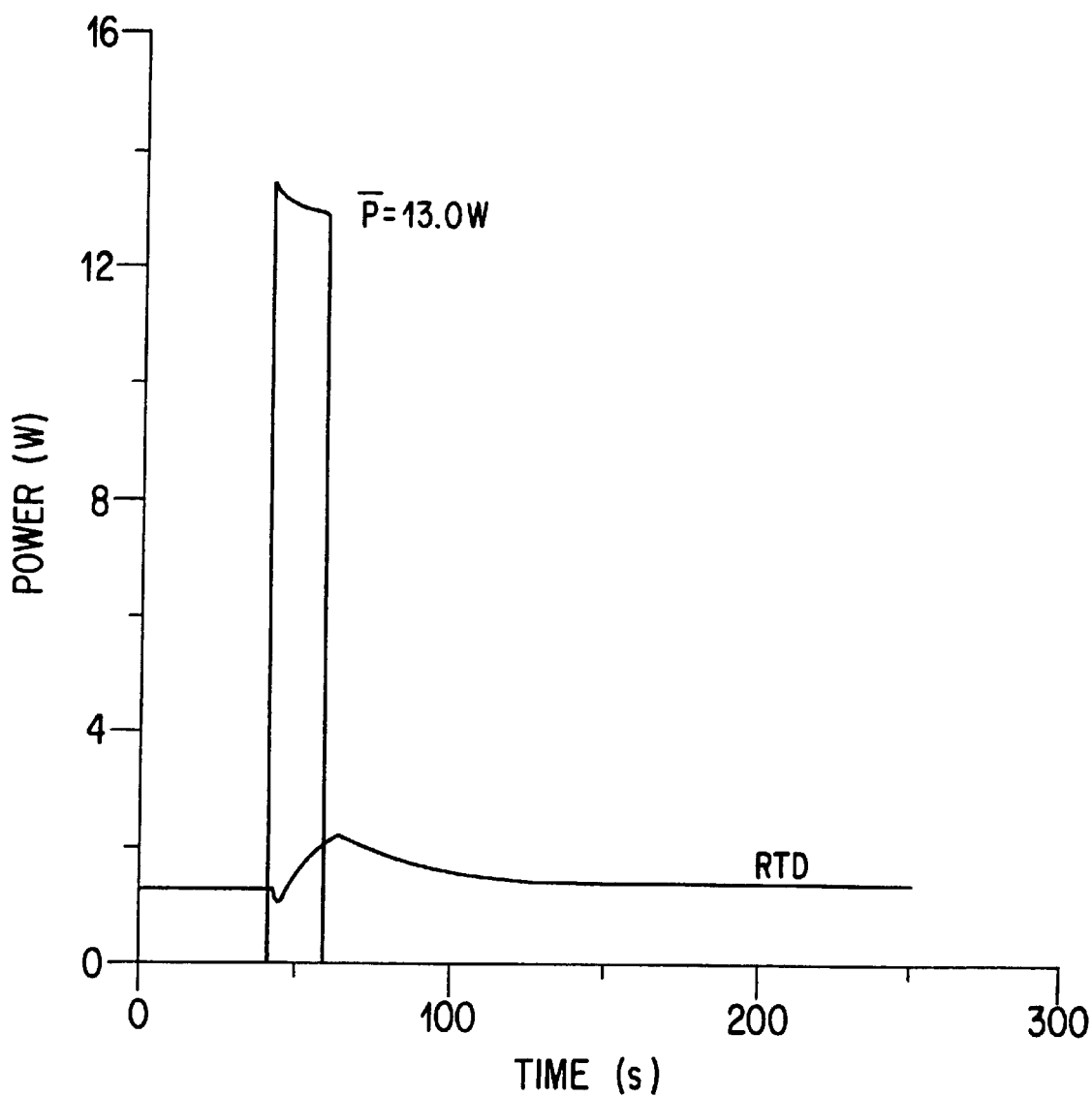
FIG. 9 is a power/time graph illustrating power consumption of the apparatus shown in FIG. 10; and, FIG. 10 is a cross-sectional view of a fifth embodiment of a gas chromatograph assembly fabricated using the apparatus shown in FIG. 1.

In operation, the assembly of FIG. 10 was heated from ambient temperature up to 270° C. in 20 seconds with an average power consumption of 13 watts during the flash heating injecting phase. The transfer line was further used extensively for a variety of chromatography measurements without any sign of failure in the electrical insulation layers of the device. Referring to the graph in FIG. 9, power measurements and RTD sensor traces are shown depicting the operation of the transfer line.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. An apparatus for applying a layer to a surface of an elongate gas chromatograph (GC) component member, comprising:

a support member having an opening formed therethrough;

drive means coupled to said support member for rotative displacement of said support member about an axis line of rotation disposed coaxially with said opening in said support member, said drive means including a first variable speed drive motor for adjustably controlling an angular speed of said support member;

dispensing means for dispensing said elongate GC component member to pass through said opening in said support member along said axis line of rotation, said dispensing means including a second variable speed drive motor for adjustably controlling a linear speed of said elongate GC component member being dispensed, said first and second variable speed drive motors being rotatively displaceable each with respect to the other in a predetermined rotative ratio;

at least one spool for dispensing at least one substantially continuous fiber therefrom, an end portion of said substantially continuous fiber being spirally wrapped around said elongate GC component member; and, spindle means mounted to said support member for coupling said at least one spool to said support member at a predetermined radial distance away from said axis line of rotation, said substantially continuous fiber being dispensed responsive to said rotative displacement of said support member to progressively wrap said substantially continuous fiber around said elongate GC component member as said elongate GC component member is dispensed, a predetermined coverage density of said substantially continuous fiber being established responsive to adjustment of said angular speed of said support member responsive to the rotative speed of said first variable speed motor and adjustment of said linear speed of said elongate GC component member being dispensed to produce a corresponding predetermined ratio between said angular speed of said support member and said linear speed of said elongate GC component member being selectively dispensed responsive to said predetermined rotative ratio between said first and second variable speed motors.

2. The apparatus as recited in claim 1 where said at least one substantially continuous fiber is a ceramic roving.

3. A method for applying an electrical insulating layer to a surface of GC component member, including the steps of:

providing at least one elongate GC component member extending in a predetermined direction;

adjusting a GC component member drive motor to progressively displace said elongate GC component member at a predetermined linear speed along said predetermined direction;

providing at least one substantially continuous ceramic fiber roving;

providing at least one dispensing means for dispensing said at least one substantially continuous ceramic fiber roving therefrom responsive to rotation of said dispensing means about said elongate GC component member;

rotatively displacing said at least one dispensing means about said progressively advancing elongate GC component member; and, adjusting a rotation drive motor to provide an angular speed of said at least one dispensing means to obtain a predetermined ratio between said angular speed of said at least one dispensing means and said linear speed of said elongate GC component member, whereby said surface of said elongate GC component member is progressively wound with said at least one ceramic fiber roving at a predetermined coverage density.

* * * * *